US008374414B2

(12) United States Patent
Tang et al.

(10) Patent No.: US 8,374,414 B2
(45) Date of Patent: Feb. 12, 2013

(54) METHOD AND SYSTEM FOR DETECTING ISCHEMIC STROKE

(75) Inventors: Fuk Hay Tang, Hong Kong (HK); Kei Shing Ng, Hong Kong (HK); Hung Kay Chow, Hong Kong (HK)

(73) Assignee: The Hong Kong Polytechnic University, Hung Hom, Kowloon (HK)

( * ) Notice: Subject to any disclaimer, the term of this patent is extended or adjusted under 35 U.S.C. 154(b) by 337 days.

(21) Appl. No.: 12/940,059

(22) Filed: Nov. 5, 2010

(65) Prior Publication Data

US 2012/0114205 A1    May 10, 2012

(51) Int. Cl.
    *G06K 9/00*    (2006.01)
(52) U.S. Cl. .......................................... 382/131; 382/283
(58) Field of Classification Search .................. None
    See application file for complete search history.

(56) References Cited

U.S. PATENT DOCUMENTS

| 2006/0056691 | A1* | 3/2006 | Vaz et al. ....................... 382/173 |
| 2009/0279752 | A1* | 11/2009 | Sirohey et al. .................. 382/128 |
| 2010/0021035 | A1* | 1/2010 | Gupta et al. ................... 382/131 |

FOREIGN PATENT DOCUMENTS

| WO | WO 2006028416 | * | 3/2006 |
| WO | WO 2008069762 | * | 12/2007 |

OTHER PUBLICATIONS

Chawla, M. and Sharma, S. and Sivaswamy, J. and Kishore, LT. A method for automatic detection and classification of stroke from brain CT images. Engineering in Medicine and Biology Society, 2009. EMBC 2009, Annual International Conference of the IEEE, Sep. 2009.*
Vogelsang F, Weiler F, Dahmen J, Kilbinger M, WeinB, Günther R. Detection and compensation of rib structures in chest radiographs for diagnose assistance. Proc Soc Photo Opt Instrum Eng. 1998; 3338: 774-785.
Maroulis DE, Savelonas MA, Karkanis SA, Iakovidis DK, Dimitropoulos N. Computer-aided thyroid module detection in ultrasound images, 18th IEEE Symposium on Computer-Based Medical Systems (CBMS'05). 2005; p. 271-276.
Byun J, Verardo MR, Sumengen B, Lewis GP, Manjunath BS, Fisher SK. Automated tool for the detection of cell nuclei in digital microscopic images: application to retinal images. Mol Vis. 2006,.12:949-960.
Liao CC, Xiao F, Wong JM, Chiang IJ. A simple genetic algorithm for tracing the deformed midline on a single slice of brain CT using quadratic Bézier curves. In: 6th IEEE International Conference on Data Mining Workshops. New York: IEEE Press. 2006; p. 463-467.

(Continued)

*Primary Examiner* — Bhavesh Mehta
*Assistant Examiner* — Tahmina Ansari
(74) *Attorney, Agent, or Firm* — The Hong Kong Polytechnic University (57) ABSTRACT

A method for assisting diagnosis of stroke by image analysis, the method comprising obtaining a scanned brain image of a patient, transforming the scanned brain image into a digitized brain image, removing bone and other artifacts from the digitized brain image, generating at least one circular adaptive region of interest on one side of the brain image, generating a binary mask of the circular adaptive region of interest, calculating the percentage of zeros from the binary mask within the circular adaptive region of interest, locating at least one corresponding circular adaptive region of interest on the other side of the brain image, and comparing the circular adaptive region of interest with the corresponding circular adaptive region on interest of the other side of the brain based on a plurality of texture attributes.

17 Claims, 9 Drawing Sheets

OTHER PUBLICATIONS

Thom T, Haase N, Rosamond W, Howard VJ, Rumsfeld J, Manolio T, et al. Heart disease and stroke statistics—2006 update: a report from the American Heart Association Statistics Committee and Stroke Statistics Subcommittee. Circulation. 2006; 113:e85-e151.

de Haan RJ, Limburg M, Van der Muelen JHP, Jacobs HM, Aaronson NK. Quality of life after stroke: impact of stroke type and lesion location. Stroke. 1995; 26:402-408.

Adams, HP, Adams R., del Zoppo G, Goldstein, LB. Guidelines for the early management of patients with ischemic stroke: 2005 guidelines update. Stroke; 2005; 36(4), 916-921.

Toni D, Iweins F, von Kummer R, Busse O, Bogousslavsky J, Falcou A, E, Lesaffre E, Lenzi GL. Identification of lacunar infarcts before thrombolysis in the ECASS 1 Study. Neurology. 2000; 54: 684-688.

Winbeck K, Bruckmaier K, Etgen T, von Einsiedel HG, Röttinger M, Sander D. Transient Ischemic Attack and Stroke Can Be Differentiated by Analyzing Early Diffusion-Weighted Imaging Signal Intensity Changes. Stroke. 2004; 35:1095.

Talairach J,Tournoux P, A Co-Planar Stereotaxic Atlas of the Human Brain: An Approach to Medical Cerebral Imaging, Thieme, New York, 1988.

Lee Y, Takahashi N, Tsai DY, Fujita H. Detectability improvement of early sign of acute stroke on brain CT images using an adaptive partial smoothing filter. Proc Soc Photo Opt Instrum Eng Med Imaging. 2006; 6144: 2138-2145.

Przelaskowski A, Sklinda K, P. Bargiel P, J. Walecki J, Biesiadko-Matuszewska M, Kazubek M. Improved early stroke detection: wavelet-based perception enhancement of computerized tomography exams. Comp Biol Med. 2007; 37:524-533.

Chawla, M. and Sharma, S. and Sivaswamy, J. and Kishore, LT. A method for automatic detection and classification of stroke from brain CT images. Engineering in Medicine and Biology Society, 2009. EMBC 2009. Annual International Conference of the IEEE, 2009.

Chan T. Computer aided detection of small acute intracranial hemorrhage on computer tomography of brain, Computerized Medical Imaging and Graphics. 2007 June-July; 07(4-5): 285-298.

Truwit CL, Barkovich AJ, A Gean-Martin, N. Hibrin, D Norman. Loss of the insular ribbon: another sign of CT infarction. Radiology. 1990; 176:801-806.

Tomura N, Uemura K, Inugami A, Fujita H, Higano S, Shishida F. Early CT finding in cerebral infarction: obscuration of the lentiform nucleus. Radiology 168:463-467, 1988.

Bozzao L, Bastianello S, Fantozzi L, Angeloni U, Argentino C, Fieschi C. Correlation of angiographic and sequential CT findings in patients with evolving cerebral infarction. AJNR Am J Neuroradiol. 1989; 10:1215-1222.

Gács G, Fox AJ, HJ Barnett, F Viñuela. CT visualization of intracranial arterial thromboembolism. Stroke. 1983; 14:756-762.

van den Bergh F, Meertens H, Moonen L, van Bunningen B, Blom A. The use of a transverse CT image for the estimation of the dose given to the rectum in intracavitary brachytherapy for carcinoma of the cervix. Radiother Oncol. 1998;47(1):85-90.

Cheng, LL, Chang IW, Louis DN, Gonzalez RG. Correlation of High-Resolution Magic Angle Spinning Proton Magnetic Resonance Spectroscopy with Histopathology of Intact Human Brain Tumor Specimens. Cancer Research.1998. 58:1825-1832.

Cheng HD, Cai XP, Chen XW, Hu LM, Lou XL. Computer-aided detection and classification of microcalcifications in mammograms: a survey. Pattern Recognition. 2003; 36: 2967-2991.

Ferro JM, Canhao P, Stam J, Bousser MG, Barinagarrementeria F. Prognosis of cerebral vein and dural sinus thrombosis (ISCVT). Stroke. 2004;35:664-70.

Haralick RM, Shanmugam K, Dinstein I. "Textural Features for Image Classification". IEEE Transactions on Systems, Man, and Cybernetics SMC-3. 1973; (6): 610-621.

Doi K. Current status and future potential of computer-aided diagnosis in medical imaging, Br J Rad, Special Issue. 2005; 78:S3-S19.

Verikas A, Gelzinis A,Bacauskiiene M, Uloza V. Towards a computer-aided diagnosis system for vocal cord diseases, Artif Intell Med. 2006. 36(1):71-84.

* cited by examiner

$$I = \begin{bmatrix} 117 & 117 & 115 & 115 & 120 & 120 & 118 & 119 & 118 & 117 & 118 & 117 & 116 \\ 118 & 118 & 116 & 117 & 118 & 118 & 117 & 120 & 117 & 116 & 115 & 118 & 116 \\ 117 & 117 & 118 & 119 & 120 & 117 & 119 & 120 & 119 & 120 & 118 & 117 & 117 \\ 118 & 116 & 118 & 116 & 118 & 116 & 118 & 120 & 117 & 118 & 120 & 118 & 119 \\ 118 & 120 & 119 & 117 & 117 & 117 & 116 & 119 & 120 & 117 & 116 & 115 & 117 \\ 119 & 117 & 117 & 119 & 120 & 120 & 116 & 116 & 117 & 119 & 119 & 118 & 118 \\ 117 & 120 & 118 & 119 & 120 & 118 & \boxed{\begin{array}{c} I(x_c, y_c) \\ = \boxed{119} \end{array}} & 119 & 118 & 117 & 118 & 116 & 118 \\ 116 & 118 & 115 & 117 & 117 & 118 & 119 & 118 & 118 & 116 & 118 & 118 & 118 \\ 117 & 118 & 116 & 117 & 117 & 118 & 116 & 117 & 117 & 116 & 118 & 118 & 117 \\ 117 & 116 & 118 & 118 & 120 & 119 & 119 & 116 & 117 & 118 & 117 & 118 & 117 \\ 119 & 120 & 116 & 117 & 120 & 117 & 116 & 118 & 118 & 117 & 119 & 119 & 118 \\ 118 & 116 & 119 & 118 & 119 & 117 & 115 & 118 & 117 & 118 & 118 & 117 & 118 \\ 116 & 115 & 118 & 120 & 117 & 116 & 119 & 120 & 119 & 120 & 118 & 118 & 119 \end{bmatrix}$$

FIG. 4A $$B_6 = \begin{bmatrix} 1 & 1 & 0 & 0 & 0 & 1 & 1 & 1 & 1 & 1 & 1 & 1 & 1 \\ 1 & 1 & 1 & 1 & 1 & 1 & 1 & 1 & 1 & 1 & 0 & 1 & 1 \\ 1 & 1 & 1 & 1 & 1 & 1 & 1 & 1 & 1 & 1 & 1 & 1 & 1 \\ 1 & 1 & 1 & 1 & 1 & 1 & 1 & 1 & 1 & 1 & 1 & 1 & 1 \\ 1 & 1 & 1 & 1 & 1 & 1 & 1 & 1 & 1 & 1 & 1 & 0 & 1 \\ 1 & 1 & 1 & 1 & 1 & 1 & 1 & 1 & 1 & 1 & 1 & 1 & 1 \\ 1 & 1 & 1 & 1 & 1 & 1 & 1 & 1 & 1 & 1 & 1 & 1 & 1 \\ 1 & 1 & 0 & 1 & 1 & 1 & 1 & 1 & 1 & 1 & 1 & 1 & 1 \\ 1 & 1 & 1 & 1 & 1 & 1 & 1 & 1 & 1 & 1 & 1 & 1 & 1 \\ 1 & 1 & 1 & 1 & 1 & 1 & 1 & 1 & 1 & 1 & 1 & 1 & 1 \\ 1 & 1 & 1 & 1 & 1 & 1 & 1 & 1 & 1 & 1 & 1 & 1 & 1 \\ 1 & 1 & 1 & 1 & 1 & 0 & 1 & 1 & 1 & 1 & 1 & 1 & 1 \\ 1 & 0 & 1 & 1 & 1 & 1 & 1 & 1 & 1 & 1 & 1 & 1 & 1 \end{bmatrix}$$

METHOD AND SYSTEM FOR DETECTING ISCHEMIC STROKE

BACKGROUND OF THE INVENTION

1. Field of the Invention

The present invention relates to a method and system for analyzing medical image data, more particularly, detecting ischemic stroke by comparing texture attributes of image data.

2. Description of the Related Art

With aging of our population, stroke has been rated the third highest cause of death in the world. Ischemic stroke occurs as a result of blood clot or thrombus in an artery or the development of fatty deposits lining the vessel walls. A computer-aided detection (CAD) scheme can be served as an alert system for detection of abnormality that may easily be overlooked by clinicians or a tool to improve the accuracy of diseases detection. The use of mathematical models for computer-aided detection (CAD) has achieved certain success in the radiological science.

Strokes can be broadly divided into hemorrhagic and ischemic strokes from management point of view. A lacunar stroke is a subtype of ischemic stroke. It is a blockage of blood flow to apart of the brain supplied by one or more small arteries. This type of stroke is relatively difficult to identify, as it manifests as a small hypodense area of less than 15 mm in diameter.

Clinically, Computed Tomography (CT) remains the choice for evaluation of patients with suspected acute ischemic stroke because CT is more accessible, inexpensive, efficient and reliable method to obtain images of a body parts. Since an accurate imaging diagnosis is critical for a patient's survival, it is desirable to establish a computer-aided system for early detection of ischemic stroke.

Clinical diagnosis of lacunar stroke is difficult if the assessment is based on features appear within first few hours after the onset of stroke. Winbeck et al., "*Transient Ischemic Attack and Stroke Can Be Differentiated by Analyzing Early Diffusion-Weighted Imaging Signal Intensity Changes*", describes that small lesion might be missed even on high resolution diffusion-weighted imaging (DWI). Therefore, early detection of lacunar stroke is crucial and this necessitates a more efficient method to improve the detection rate.

Previous attempts have been made for the detection of acute stroke such as normalization of the CT image into a standard atlas to identify hypodensity within the insula ribbon and lentiform nucleus (Talairach et al., "*A Co-Planar Stereotaxic Atlas of the Human Brain: An Approach to Medical Cerebral Imaging*", Thieme); applying an adaptive partial smoothing filter (APSF) (Lee et al., "*Detectability improvement of early sign of acute stroke on brain CT images using an adaptive partial smoothing filter*") to reduce noise component and enhance important signal components; using wavelet-based image processing to improve the contrast and denoise the subtle signs of hypodensity of the image locally (Przelaskowski, et al., "*Improved early stroke detection: wavelet-based perception enhancement of computerized tomography exams*").

Also, there was an attempt to use wavelet decomposition of the histogram and difference of energy measure to detect ischemic stroke (Chawla, et al., "*A method for automatic detection and classification of stroke from brain CT images*"). However, their sample size was still too small to substantiate a valid fully automatic method. Thus, a CAD scheme for automatic detection of ischemic stroke still needs further elaborations and improvements.

SUMMARY OF THE INVENTION

According to an aspect of the present invention, the present invention provides a method for assisting diagnosis of stroke by image analysis, the method comprising obtaining a scanned brain image of a patient, transforming the scanned brain image into a digitized brain image, removing bone and other artifacts from the digitized brain image, generating at least one circular adaptive region of interest with a center ($X_c$, $Y_c$) and radius r on one side of the brain image, generating a binary mask of the circular adaptive region of interest, calculating the percentage of zeros ($P_0$) from the binary mask within the circular adaptive region of interest, increasing the radius of the circular adaptive region of interest if $P_0$ is greater than a cutoff value, locating at least one corresponding circular adaptive region of interest on the other side of the brain image, and comparing the circular adaptive region of interest with the corresponding circular adaptive region on interest of the other side of the brain based on a plurality of texture attributes.

According to another aspect of the present invention, a system for assisting diagnosis of stroke by image analysis, comprising an image capture device configured to obtain a scanned brain image of a patient, transform the scanned brain image into a digitized brain image, and transmit the digitized brain image; an image analyzing unit configured to receive the digitized brain image, remove bone and other artifacts from the digitized brain image, generate at least one circular adaptive region of interest with a center ($X_c$, $Y_c$) and radius r on one side of the brain image, generating a binary mask of the circular adaptive region of interest, calculating the percentage of zeros ($P_0$) from the binary mask within the circular adaptive region of interest, increase the radius of the circular adaptive region of interest if $P_0$ is greater than a cutoff value, locating at least one corresponding circular adaptive region of interest on the other side of the brain image, and compare the circular adaptive region of interest with the corresponding circular adaptive region on interest of the other side of the brain based on a plurality of texture attributes.

Further features and aspects of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

FIGS. 4A and 4B illustrate generation of a binary mask according to an embodiment of the present invention.

DESCRIPTION OF THE EMBODIMENTS

Embodiments of the present invention will be described in detail in accordance with the accompanying drawings.

A system for assisting early diagnosis of injury due to ischemic stroke is disclosed herein. Identifying ischemic stroke from CT scan within a few hours after onset of stroke can be difficult. In most cases, CT signs of stroke can only be apparent after 24 hours of an onset of ischemic stroke. Early detection relied on some important early abnormal signs, including loss of the insular ribbon, attenuation of the lentiform nucleus (ALN), hemispherical sulcus effacement (HSE), and the hyperdense middle cerebral artery sign (HM-CAS). The present invention incorporates these features into the CAD scheme so as to detect the early sign of ischemic stroke.

Figure 1A:
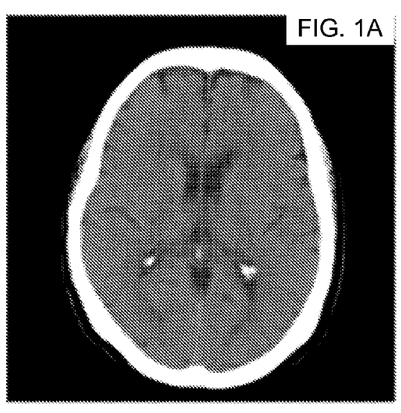
FIGS. 1A and 1B illustrate a scanned brain image.
Figure 1B:
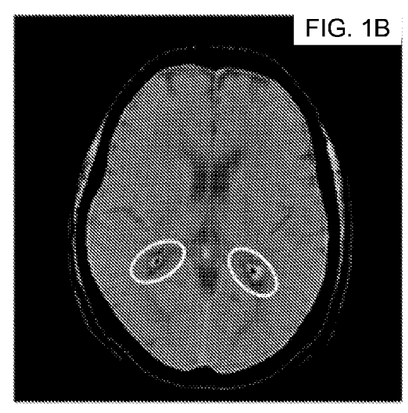

First, a brain image from a CT scan is obtained. The image may be in a digital format such as a DICOM (Digital Imaging and Communications in Medicine) format. In order to view abnormality inside the brain, the bony skull and scanning artifact is removed. For example, scanning artifact can be removed by global thresholding method as disclosed in Chan Tao's "*Computer aided detection of small acute intracranial hemorrhage on computer tomography of brain*", the information thereof is incorporated herein by reference. FIG. 1 is a slice of a CT scan image of a patient's brain. Thus, segmentation of the cranial content of the brain is performed to remove structures not contiguous with the main central bulk of cranial contents such as scalp, orbits, and other head and neck soft tissues. The brain image is then realigned to a normal position. As shown in FIG. 1A, prior to performing global thresholding, the bone and other artifacts remain in the scanned brain image. FIG. 1B illustrates an image after global thresholding is performed. While the bone and other artifacts are removed from the image, several regions of calcification are also removed, as indicated in the circled region of FIG. 1B. However, these regions of calcification may be useful for further image analysis, and thus, these calcifications shall be preserved.

Figure 2:
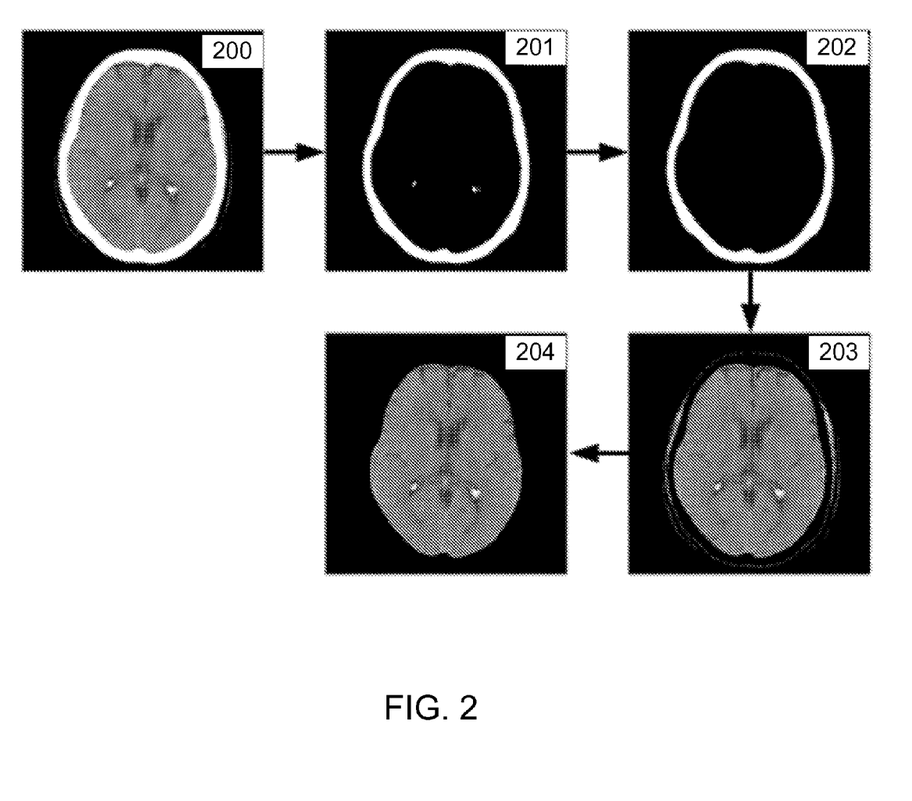
FIG. 2 illustrates the process for removing bone and other artifacts from a scanned brain image.

FIG. 2 illustrates a method for removing unwanted regions such as bones and other small artifacts in accordance with one embodiment of the present invention. In step 201, the CT scan image 200 is transformed into a binary image. Next, the regions of calcification with fewer than a certain number of pixels are removed (step 202). For example, the regions of calcifications with fewer than 500 square pixels are removed. In step 203, the bone is removed in reference to the binary image. Since there are small external structures surrounding the perimeter of the intracranial content, these small external structures are removed. Step S204 shows an exemplary image after removing the unwanted regions.

Figure 3:
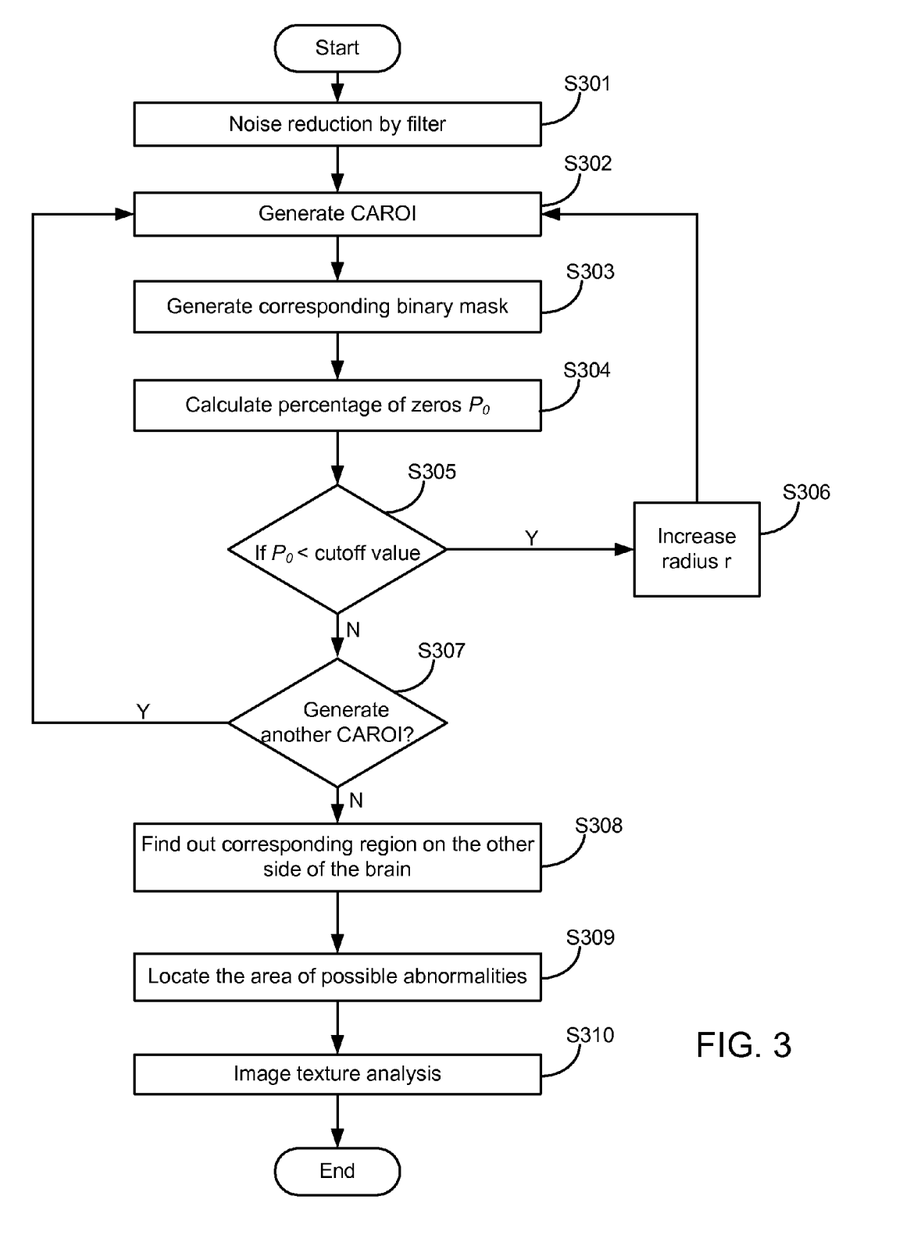
FIG. 3 illustrates an exemplary process flow for analyzing abnormalities in a scanned brain image.

FIG. 3 illustrates an exemplary process flow for analyzing abnormalities in a scanned brain image. The process begins with one side of the brain. In this embodiment, the process begins with the left side of the brain. An image showing areas where blood clot often occurs shall be obtained, for example, an image showing the brain anterior cerebral artery (ACA), middle cerebral artery (MCA), and posterior cerebral artery (PCA), and basal ganglia is obtained to locate the region with subtle change of intensity.

In step S301, noise reduction is performed on a scanned brain image by filtering. For example, a 3×3 filtering is performed on the image, $$I * \frac{1}{9} \begin{bmatrix} 1 & 1 & 1 \\ 1 & 1 & 1 \\ 1 & 1 & 1 \end{bmatrix} \quad (1)$$

Where I is the sectional CT images and * is an image convolution operator. The filter is applied to the image so as to improve its image quality in term of peak signal-to-noise (PSNR) ratio. The typical values for PSNR range between 30-50 dB, the higher the value of PSNR, the better the image quality.

In step S302, a circular adaptive region of interest (hereinafter refers to as CAROI) is generated. The initial radius r of the CAROI is 5 pixels because the typical size of the blood clot associated with a lacunar stroke is approximately 15 mm wide. Since the image resolution is about 3 mm per pixel, a radius of 5 is selected as the initial value. Depending on the pixel size, the radius of the CAROI can be changed.

A center point $(X_c, Y_c)$ is obtained by the computer on the left side of the brain. The center point may be located where blood clot most often occurs such as ACA, MCA, PCA, or basal ganglia. FIG. 3 shows a CAROI with radius r=5 pixels, and therefore, the diameter of the initial circle is (2r+1) pixels.

For each point inside the circle of radius r, i.e., $\|(i, j)-(x_c, y_c)\| \leq r$, a binary mask $B_r$ is generated based on the following criteria (step S303):

$$B_r(i, j) = \begin{cases} 0, & |I(i, j) - I(x_c, y_c)| > T, \\ 1, & |I(i, j) - I(x_c, y_c)| \leq T \end{cases} \quad (2)$$

where $I(i, j)$ is the pixel value (intensity) of pixel $(i, j)$. Thus, when $|I(i, j)-I(X_c, Y_c)|$ is less than or equal to a threshold value T, a binary mask value of "1" is assigned; when $|I(i, j)-I(X_c, Y_c)|$ is greater than a threshold value T, a binary mask value of "0" is assigned. In the example illustrate in FIGS. 4A and 4B, a threshold value of 3 is used. While the present example uses a threshold value of "3", another threshold value may be utilized. FIG. 4A displays the intensity of a region of interest with center $(X_c, Y_c)$ in a matrix. FIG. 4B illustrates the result of using equation (2) of an object region (mask value 1) and background region (mask value 0).

Figure 5:
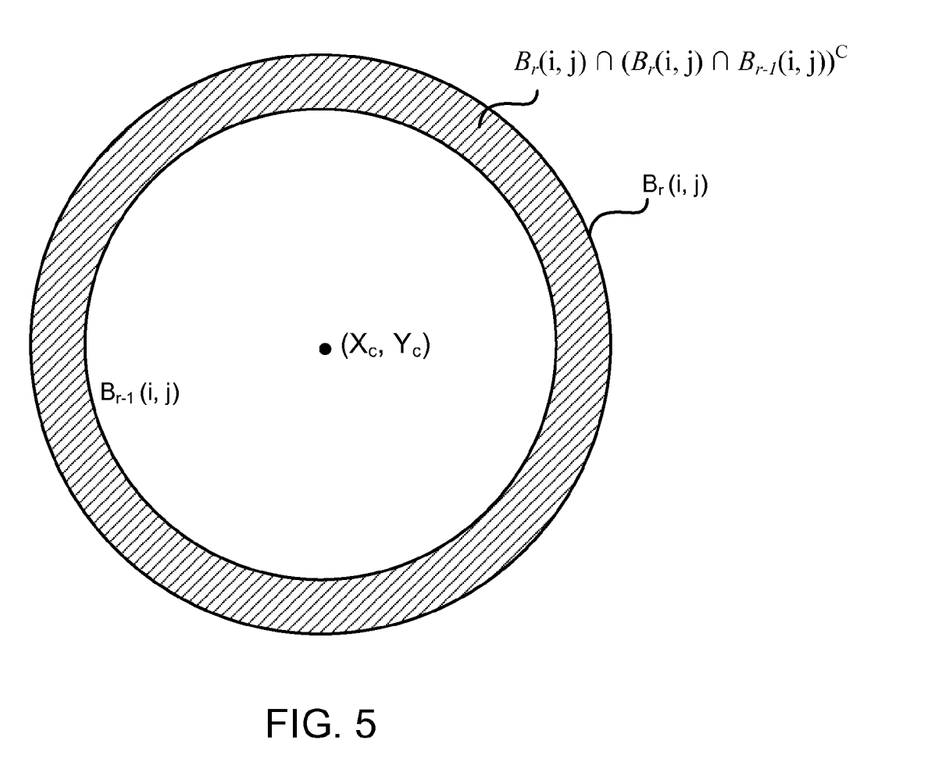
FIG. 5 illustrates a circular band of boundary image.
Figure 6:
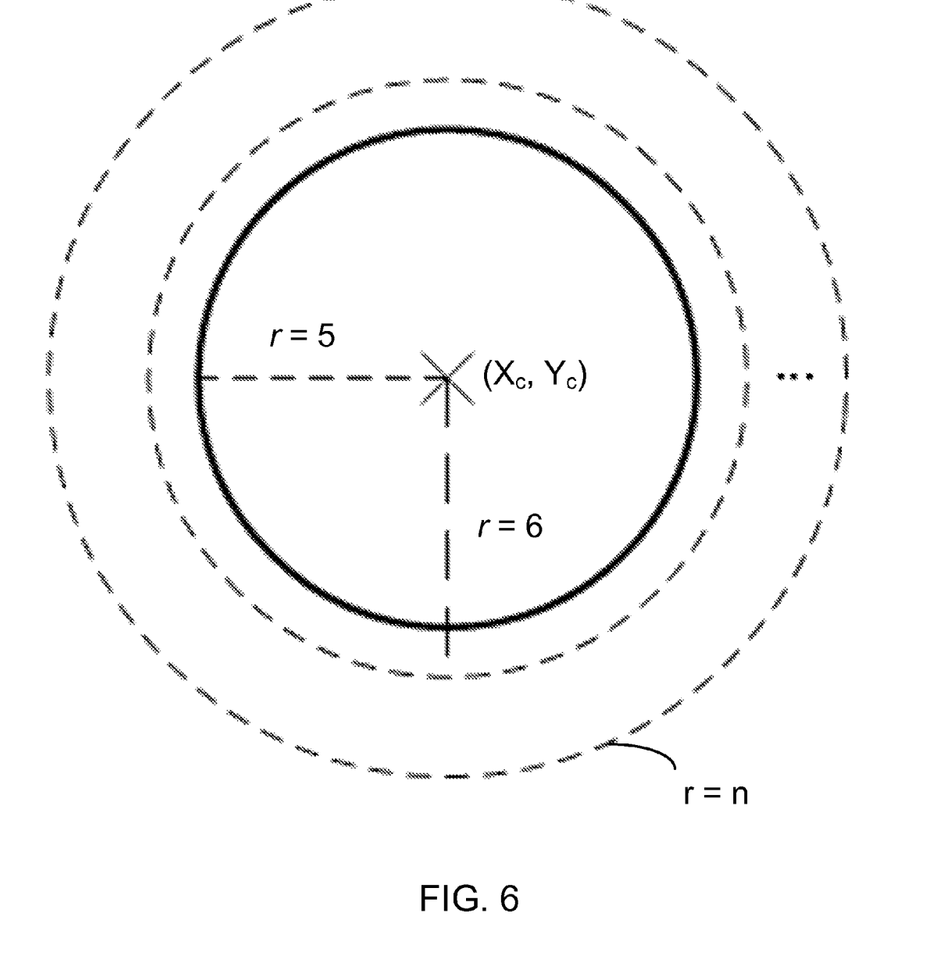
FIG. 6 illustrates an exemplary circular adaptive region of interest.

Then, the percentage of zeros $(P_0)$ over the binary mask is calculated in step S304 using the following equation:

$$P_0 = \frac{\sum_{B_r(i,j) \cap (B_r(i,j) \cap B_{r-1}(i,j))^C = 0} (1 - B_{r+1})}{\sum_{B_r(i,j) \cap (B_r(i,j) \cap B_{r-1}(i,j))^C = 0,1} 1} \times 100\% \quad (3)$$

where $B_r(i, j) \cap (B_r(i, j) \cap B_{r-1}(i, j))^C$ is referred to the boundary region of the binary mask, as indicated in the shaded region of FIG. 5.

Step S305 determines whether $P_0$ is less than a cut-off value. In this embodiment, the cut-off value of $P_0$ in step S305 is chosen as 60% indicating the adaptive region of interest is non-homogeneous, i.e., a significant difference in intensity between the center-point $(X_c, Y_c)$ and the points over the boundary. The cut-off value is not limited to any particular percentage. If $P_0$ is less than the cut-off value (Yes in step S305), the process advances to step S306 to increase the radius r. For instance, as shown in FIG. 4, as the radius increase, the CAROI is also increased. Then, the flow returns to step S302. If $P_0$ is greater than or equal to the cut-off value, the process advances to step S307 to determine whether to generate another CAROI with a different center point. If it is determined that another CAROI shall be generated, the process returns to step S302 to generate another CAROI. Otherwise, the process advances to step S308.

For each CAROI generated on the left side, a corresponding circle(s) on the left side shall be found (S308). The contralateral side of the brain can be regarded as a reflection from the other side of the brain. Hence, the lateral reflection of the adaptive circle on the other side of the brain can be obtained. Then, the corresponding location of CARIO is searched, for example, by best matching using Pearson's correlation coefficient R. For binarized digital image, the Pearson correlation coefficient can be defined as, $$R = \frac{\sum_i (p_i - p_m)(q_i - q_m)}{\sqrt{\sum_i (p_i - p_m)^2} \sqrt{\sum_i (q_i - q_m)^2}}$$

where $p_i$ is the intensity of the $i^{th}$ pixel in circle at the right side of the brain and $q_i$ is the intensity of the $i^{th}$ pixel at the flipped left side of the brain, $p_m$ and $q_m$ is the mean intensity at the right side and flipped left side of the brain respectively. The correlation coefficient has the value of "1" if the two images are identical and a value of "0" if the two images are not correlated. Next, the corresponding CAROI with least correlation is located at the other side of the brain in S309.

In step S310, the CAROI of the right side is compared with the corresponding CAROI of the left side of the brain. The comparison can be realized by using Texture Analysis (TA). For example, using texture analysis method to analyze the images features are disclosed in Cheng et al., "*Computer-aided detection and classification of microcalcifications in mammograms*", and Ferro et al., "*Prognosis of cerebral vein and dural sinus thrombosis* (ISCVT)". Grey level co-occurrence matrix (GLCM) can be used to extract the information from an image. For example, given an images of size m×n, parameterized by an offset ($\Delta x$, $\Delta y$) the co-occurrence matrix of size 8×8 can be calculated as:

$$C(i,j) = \sum_{p=1}^{m} \sum_{q=1}^{n} \begin{cases} 1, & \text{if } I(p,q) = i \text{ and } I(p + \Delta x, q + \Delta y) = j, \\ 0, & \text{otherwise.} \end{cases}$$

C(i,j) represents how often a pixel with the intensity (gray-level) value i occurs in a specific spatial relationship to a pixel with the value j, and thus, other spatial relationships between two pixels can be specified.

Figure 9:
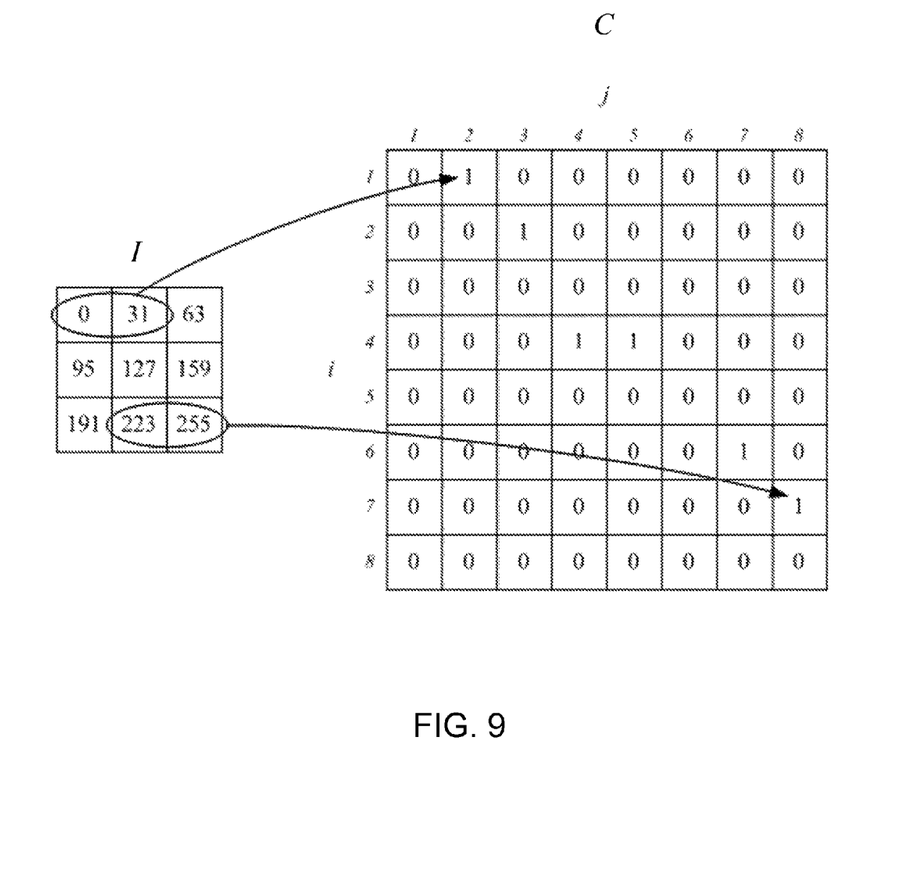
FIG. 9 shows an example of a 3×3 grayscale image I can be transformed into a gray-level co-occurrence matrix C.

FIG. 9 shows how a 3×3 grayscale image I can be transformed into a gray-level co-occurrence matrix C. Image I with intensity level 0-255 is scaled to 8 levels. Element (1, 2) in the GLCM C has a value of "1" because there is only one instance in the input image where two horizontally adjacent pixels have level 1 and level 2.

Based on the information of the co-occurrence matrix, we could apply the histogram statistics, as disclosed in "*Textural Features for Image Classification*" (Haralick et al, 1973), to produce texture attributes. The texture attributes can be derived from the co-occurrence matrix and they are denoted by A1-A8 as follows:

$$\text{Energy: } \sum_{i,j} C(i,j)^2 \tag{A1}$$

$$\text{Entropy: } -\sum_{i,j} C(i,j)\log C(i,j) \tag{A2}$$

$$\text{Inverse difference moment: } \sum_{i,j} \frac{1}{1+(i-j)^2} C(i,j) \tag{A3}$$

$$\text{Inertia: } \sum_{i,j} (i-j)^2 C(i,j) \tag{A4}$$

$$\text{Shade: } \sum_{i,j} (i+j-\mu_x-\mu_y)^3 C(i,j) \tag{A5}$$

$$\text{Prominence: } \sum_{i,j} (i+j-\mu_x-\mu_y)^4 C(i,j) \tag{A6}$$

$$\text{Correlation: } -\sum_{i,j} \frac{(i-\mu_x)+(j-\mu_y)}{\sqrt{(\sigma_x \sigma_y)}} C(i,j) \tag{A7}$$

$$\text{Variance: } \sum_{i,j} (i-u)^2 C(i,j) \tag{A8}$$

where $\mu_x$, $\mu_y$, $\sigma_x$ and $\sigma_y$ represent the mean and standard deviation of row or column sum respectively and $\mu$ represented the mean of the co-occurrence matrix.

The energy of a texture of an image describes the uniformity of the texture. In a homogeneous image (i.e., region with the same level of intensity), the GLCM had fewer entries of large magnitude and the energy of an image should be high. The entropy measured the randomness of the element. For homogeneous image, the entropy should be low. The inverse difference moment, would give a higher value when the diagonal of C was high, while the inertia would get a larger value when the C had a higher value away from the diagonal. The inertia and the inverse difference moment deliberated the distribution of grey-scales in the image. Shade and prominence were the measures of skewness of C. The image was not symmetric when shade and prominence were high.

The above attributes would be calculated between the contra-lateral sides and expressed in a row of vectors for further analysis.

$L_i$=[$A_1,A_2,A_3,A_4,A_5,A_6,A_7,A_8$], i=1,2, . . . ,N, $R_i$=[$A_1,A_2,A_3,A_4,A_5,A_6,A_7,A_8$], i=1,2, . . . ,N, where N is the total number of images.

In order to improve sensitivity and specificity, the detection rate is calculated per subject-based. Thus, a stroke index to quantify the probability of stroke. The quantification of stroke index required two phases, namely training and testing phases. To perform the training stage, 2500 sectional scans are analyzed.

For healthy subjects, the left brain shall be the same as the right brain, and consequently, the left CAROI and the right CAROI shall be the same. As such, the following ratio is expected:

$$\frac{L_i}{R_i} \approx [1, 1, 1, 1, 1, 1, 1, 1]$$

In order to increase detectability of stroke, regional replacement method and Feature Based Index (FBI) are utilized.

Figure 7:
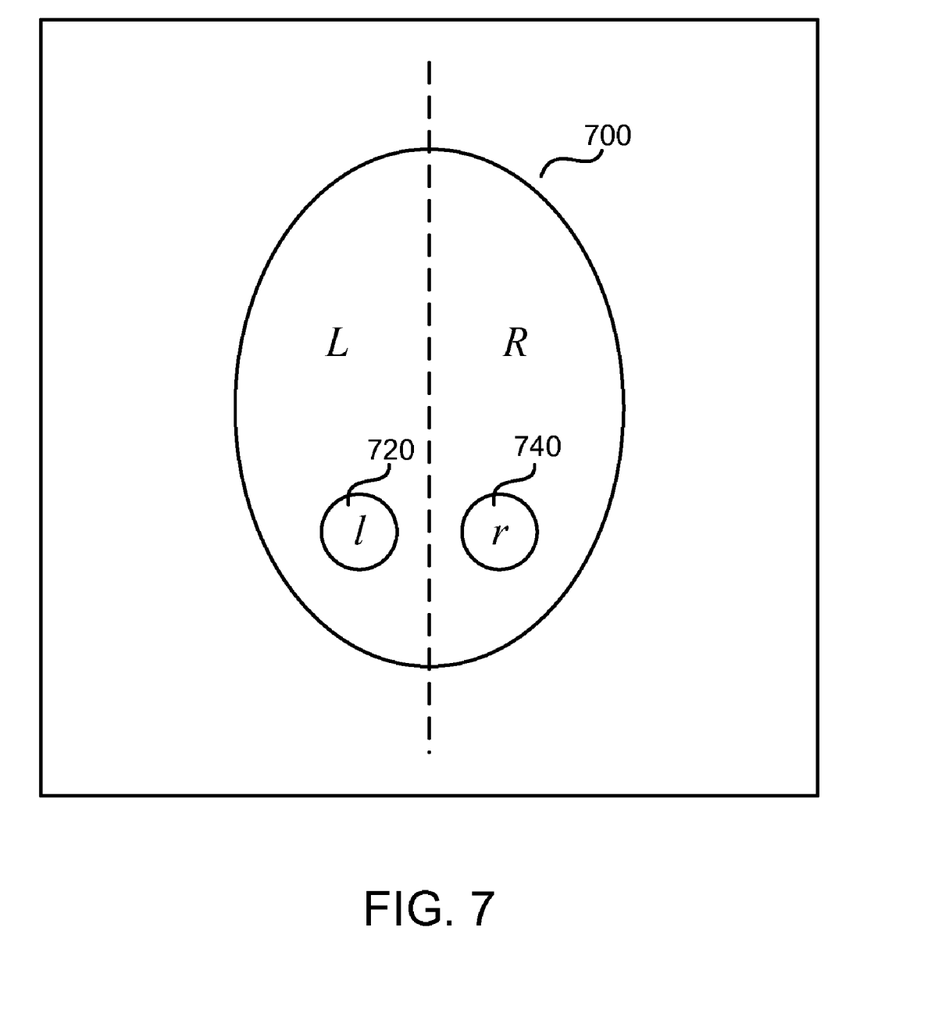
FIG. 7 illustrates an exemplary scanned image used in the regional replace method.

FIG. 7 illustrates an exemplary scanned image used for the regional replace method. In the image 700, the texture attributes (A1-A8) of the left side of the brain is denoted by L and the texture attributes of the right side of the brain is denoted by R. For each CAROI (i.e., l (720) and r (740)), $l_i \subset L$ and $r_i \subset R$. The following is calculated:

$$\frac{L}{R} \text{ and } \frac{L\setminus\{l\}}{R\setminus\{r\}}$$

If the region covered by CAROI is normal, the relative absolute change of L/R is expected to be close to zero. That is, $$\frac{\left|\frac{L\setminus\{l\}}{R\setminus\{r\}} - \frac{L}{R}\right|}{\frac{L}{R}} \to 0, \text{ and } \frac{L}{R} = \frac{L\setminus\{l\}}{R\setminus\{r\}} \to 1.$$

Conversely, if $$\frac{L}{R} \to 1 \text{ and } \left|\frac{L\setminus\{l\}}{R\setminus\{r\}} - \varepsilon\right| \to 1$$

for some $\varepsilon > 0$, ($\varepsilon$ is the error produced by image features when the CAROI of left and right obtained unequal image feature attributes) then, it is expected that the CAROI contains abnormality. This would be identified using feature based index. The whole process was repeated for all CAROI. Therefore, FBI is defined as an indicator to detect the abnormality by checking $$FBI = \frac{L}{R} \text{ and } \overline{FBI} = \frac{L\setminus\{l\}}{R\setminus\{r\}},$$

where $FBI, \overline{FBI} \in R^8$ and ,$\overline{FBI}$ were the FBI were the FBI without the CAROI for which FBI$\to$0, FBI$\to\infty$ and $\overline{FBI} \to 1$ indicate abnormality occurred at the CAROI.

Another coarse indicator was proposed to indicate whether a patient had stroke at the early stage. The following optimization problem was proposed so that every image features would be considered in the screening process in the detection of stroke.

Subject to Statistical images attributes A1 to A8. Mathematically, the clinical problem can be transformed into an optimization model Maximize the detection rate subject to 1st case →
2nd case →
3nd case →
⋮
⋮
⋮
$n$th case →
sum of all coefficient→

$$\begin{pmatrix} A_{11} & A_{12} & A_{13} & A_{14} & A_{15} & A_{16} & A_{17} & A_{18} \\ A_{21} & A_{22} & A_{23} & A_{24} & A_{25} & A_{26} & A_{27} & A_{28} \\ A_{31} & A_{32} & A_{33} & A_{34} & A_{35} & A_{26} & A_{27} & A_{38} \\ \vdots & \vdots & \vdots & \vdots & \vdots & \vdots & \vdots & \vdots \\ \vdots & \vdots & \vdots & \vdots & \vdots & \vdots & \vdots & \vdots \\ \vdots & \vdots & \vdots & \vdots & \vdots & \vdots & \vdots & \vdots \\ A_{n1} & A_{n2} & A_{n3} & A_{n4} & A_{n5} & A_{n6} & A_{n7} & A_{n8} \\ 1 & 1 & 1 & 1 & 1 & 1 & 1 & 1 \end{pmatrix}_{(n+1)\times 8} \begin{pmatrix} c_1 \\ c_2 \\ c_3 \\ \vdots \\ \vdots \\ \vdots \\ c_7 \\ c_8 \end{pmatrix}_{8\times 1} =$$

$$\begin{pmatrix} d_1 \\ d_2 \\ d_3 \\ \vdots \\ \vdots \\ \vdots \\ d_n \\ 1 \end{pmatrix}_{(n+1)\times 1} \begin{matrix} \leftarrow \text{1st output} \\ \leftarrow \text{2nd output} \\ \leftarrow \text{3rd output} \\ \\ \\ \\ \leftarrow n\text{th output} \\ \text{normalize,} \end{matrix}$$

where $A_{ij}$ represented the jth image features of ith patient, $c_j$ and $d_i$ represented the weight of the texture attribute and the result of abnormality, respectively. Since the matrix containing the image features were not square, and hence non-invertible, therefore, the present optimization problem is then transformed into the problem of least square. The coefficients of images features could be computed by left multiplying the constraints by the transpose of the matrix containing features of the image and computed the inverse directly to get the coefficients $c_j$'s. Based on the values of $c_j$'s, it could detect whether a new incoming case had stroke by computing $$d_i = A_{i1}c_1 + A_{i2}c_2 + A_{i3}c_3 + A_{i4}c_4 + A_{i5}c_5 + A_{i6}c_6 + A_{i7}c_7 + A_{i8}c_8, \; i > N.$$

For example, the d value of a normal brain can be compared with the d value of the incoming case to determine whether the incoming case has stroke.

Training the Computer-Aided Diagnostic System

In this example, 30 CT scan images are included in a sample. In particular, 10 cases are normal and 20 cases are abnormal. Of the 20 abnormal cases, 10 cases are acute ischemic stroke, and 10 cases are chronic ischemic stroke. A feed-forward back propagation Artificial Neural Network (ANN) is developed using MATLAB and the CAD scheme can be trained in a round robin manner. In the round robin method, 1 case is leave out in the testing set and the remaining 29 sets are taken as the training sets. The procedure is repeated so that each of the 30 sets are used once as the testing set.

The ANN using a round robin approach produced an estimated accuracy of 86.96%. The following table A shows the weighting of the 8 attributes determined by SPSS Clementine Version 12.

TABLE A

| Image Features | Weighting |
|---|---|
| Prominence | 0.333 |
| Correlation | 0.115 |
| Inertia | 0.111 |
| Entropy | 0.109 |
| Energy | 0.094 |
| Variance | 0.090 |

TABLE A-continued

| Image Features | Weighting |
| --- | --- |
| Inverse difference moment | 0.082 |
| Shade | 0.066 |

Figure 8:
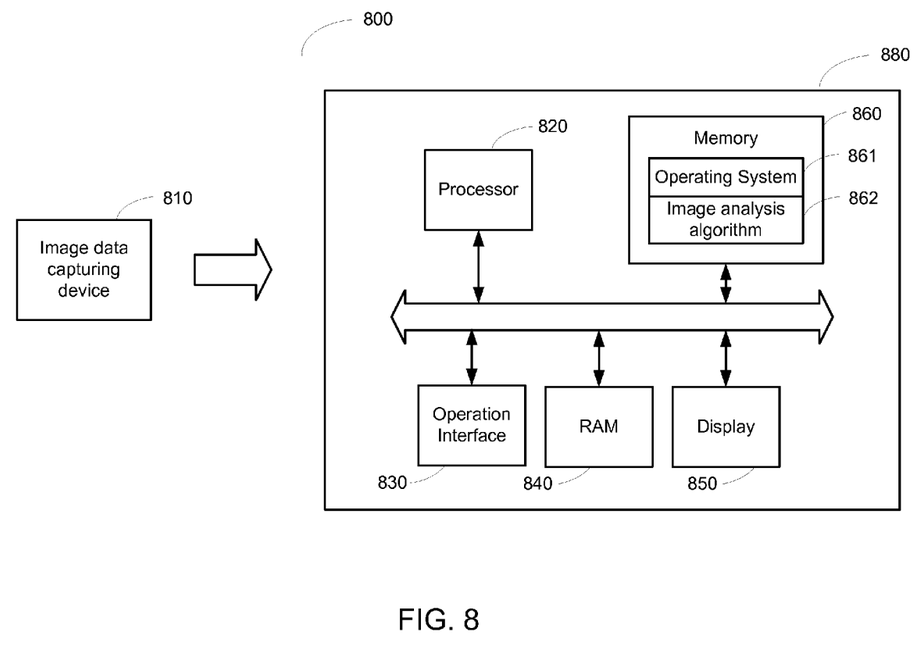
FIG. 8 illustrates an exemplary configuration of a computer-aided diagnostic system.

FIG. 8 illustrates an exemplary configuration of a computer-aided diagnostic system 800. The system includes an image data capture device 810, which may be a CT scanner, an X-ray machine or the like. The image data capture device is configured to capture brain images of a patient and transmit the captured image data to an image analyzing unit 880. It is also capable of transforming the brain image into a digital format such as a DICOM format. An image analyzing unit 880 includes a processor 820, operation interface 830, random access memory (RAM) 840, a main memory 860, and a display 850. The image data capture device 810 is a standalone device that supplies medical image data to the image analyzing unit 880 or integrated with the image analyzing unit 880 as a unit.

Memory unit 880 is a computer-readable storage device in the form of a hard disk or a flash memory that is capable of receiving, storing image data and transferring image data. In addition to storing image data, it also stores an operating system 861. Operation system 861 can be any operation system suitable for controlling the computer-aided diagnostic system 800 such as UNIX, Linux, or Microsoft Windows. It also contains computer-executable program codes (image analysis algorithm 862) for realizing the above-noted functions for image analysis.

Random access memory (RAM) 840 is a memory for temporary storing programs and the like that are read from the memory unit.

Operation interface 830 allows a user to control information on the image analyzing unit 880. The operation interface 830 may include other operation units such as a mouse, keyboard, touch screen panel, and the like for instructing the image analyzing unit 880. The display unit 850 includes a display screen for outputting information received from the image analyzing unit 880.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

What is claimed is:

1. A method for assisting diagnosis of stroke by image analysis, the method comprising:
    obtaining a scanned brain image of a patient;
    transforming the scanned brain image into a digitized brain image;
    removing bone and other artifacts from the digitized brain image;
    generating at least one circular adaptive region of interest with a center $(X_c, Y_c)$ and radius r on one side of the brain image;
    generating a binary mask of the circular adaptive region of interest;
    calculating the percentage of zeros $(P_0)$ from the binary mask within the circular adaptive region of interest;
    increasing the radius of the circular adaptive region of interest if $P_0$ is greater than a cutoff value;
    locating at least one corresponding circular adaptive region of interest on the other side of the brain image; and
    comparing the circular adaptive region of interest with the corresponding circular adaptive region on interest of the other side of the brain based on a plurality of texture attributes.

2. The method of claim 1, wherein the scanned image of the brain is a computed tomography image.

3. The method of claim 1, further comprises aligning the digitized brain image.

4. The method of claim 1, wherein the plurality of texture attributes are calculated based on grey level co-occurrence matrix, the texture attributes include energy, entropy, inverse difference moment, inertia, shade, prominence, correlation, and variance.

5. The method of claim 1, wherein locating the corresponding circular adaptive region of interest on the other side of the brain is performed by gray level co-occurrence matrix.

6. The method of claim 1, wherein removing bone and other artifacts from the digitized brain image includes removing regions of calcifications that have fewer than 500 square pixels.

7. The method of claim 1, wherein the brain image is determined as abnormal based on a Feature-Based Index (FBI), if FBI→0, FBI→∞, and $\overline{FBI}$→1,
    where $$FBI = \frac{L}{R}, \text{ and } \overline{FBI} = \frac{L\backslash\{l\}}{R\backslash\{r\}},$$

where
    L is texture attributes of a left side of the scanned brain image,
    R is texture attributes of a right side of the scanned brain images,
    l is texture attributes of the circular adaptive region of interest on the left, and
    r is texture attributes of a right side of the circular adaptive region of interest on the right side.

8. The method of claim 1, wherein the brain image shows brain anterior cerebral artery (ACA), middle cerebral artery (MCA), and posterior cerebral artery (PCA), and basal ganglia of the patient.

9. A system for assisting diagnosis of stroke by image analysis, comprising:
    an image capture device configured to obtain a scanned brain image of a patient, transform the scanned brain image into a digitized brain image, and transmit the digitized brain image;
    an image analyzing unit configured to receive the digitized brain image, remove bone and other artifacts from the digitized brain image, generate at least one circular adaptive region of interest with a center $(X_c, Y_c)$ and radius r on one side of the brain image, generating a binary mask of the circular adaptive region of interest, calculating the percentage of zeros $(P_0)$ from the binary mask within the circular adaptive region of interest, increase the radius of the circular adaptive region of interest if $P_0$ is greater than a cutoff value, locating at least one corresponding circular adaptive region of interest on the other side of the brain image, and compare the circular adaptive region of interest with the corresponding circular adaptive region on interest of the other side of the brain based on a plurality of texture attributes.

10. A non-transitory computer-readable storage medium storing a computer program that causes a computer to execute a method for assisting diagnosis of stroke by image analysis, comprising: obtaining a scanned brain image of a patient; transforming the scanned brain image into a digitized brain image; removing bone and other artifacts from the digitized brain image; generating at least one circular adaptive region of interest with a center ($X_c, Y_c$) and radius r on one side of the brain image; generating a binary mask of the circular adaptive region of interest; calculating the percentage of zeros ($P_0$) from the binary mask within the circular adaptive region of interest; increasing the radius of the circular adaptive region of interest if $P_0$ is greater than a cutoff value; locating at least one corresponding circular adaptive region of interest on the other side of the brain image; and comparing the circular adaptive region of interest with the corresponding circular adaptive region on interest of the other side of the brain based on a plurality of texture attributes.

11. The non-transitory computer-readable storage medium storing the computer program that causes the computer to execute the method of claim 10, wherein the scanned image of the brain is a computed tomography image.

12. The non-transitory computer-readable storage medium storing the computer program that causes the computer to execute the method of claim 10, further comprises aligning the digitized brain image.

13. The non-transitory computer-readable storage medium storing the computer program that causes the computer to execute the method of claim 10, wherein the plurality of texture attributes are calculated based on grey level co-occurrence matrix, the texture attributes include energy, entropy, inverse difference moment, inertia, shade, prominence, correlation, and variance.

14. The non-transitory computer-readable storage medium storing the computer program that causes the computer to execute the method of claim 10, wherein locating the corresponding circular adaptive region of interest on the other side of the brain is performed by gray level co-occurrence matrix.

15. The non-transitory computer-readable storage medium storing the computer program that causes the computer to execute the method of claim 10, wherein removing bone and other artifacts from the digitized brain image includes removing regions of calcifications that have fewer than 500 square pixels.

16. The non-transitory computer-readable storage medium storing the computer program that causes the computer to execute the method of claim 10, wherein the brain image is determined as abnormal based on a Feature-based index (FBI), if FBI→0, FBI→∞, and $\overline{FBI}$→1, where $$FBI = \frac{L}{R}, \text{ and } \overline{FBI} = \frac{L \backslash \{l\}}{R \backslash \{r\}},$$

where L is texture attributes of a left side of the scanned brain image, R is texture attributes of a right side of the scanned brain images, l is texture attributes of the circular adaptive region of interest on the left, and r is texture attributes of a right side of the circular adaptive region of interest on the right side.

17. The non-transitory computer-readable storage medium storing the computer program that causes the computer to execute the method of claim 10, wherein the brain image shows brain anterior cerebral artery (ACA), middle cerebral artery (MCA), and posterior cerebral artery (PCA), and basal ganglia of the patient.

\* \* \* \* \*